United States Patent [19]

Soukup

[11] Patent Number: 5,182,110
[45] Date of Patent: Jan. 26, 1993

[54] NATURAL EXTRACT BASED HAIR RESHAPING COMPOSITION

[76] Inventor: Vaclav Soukup, Rua Adelia, No. 140 - Apt. No. 302, Ilha do Governador, Rio de Janeiro, Brazil

[21] Appl. No.: 399,915

[22] Filed: Aug. 29, 1989

[51] Int. Cl.⁵ .............................................. A61K 35/78
[52] U.S. Cl. .................................... 424/195.1; 8/425; 8/624
[58] Field of Search ...................... 424/195.1, 425, 624

[56] References Cited

U.S. PATENT DOCUMENTS 4,801,302  1/1989  Grollier .................................. 8/624

FOREIGN PATENT DOCUMENTS 8603602  7/1986  Brazil .
717734  12/1972  South Africa .

OTHER PUBLICATIONS

Chemical Abstracts, vol. 107, No. , 1987, p. 366, 242437t, English abstract of Br. 80 03,602.
Chemical Abstract, vol. 76, #16, #89955e.

Primary Examiner—Jose G. Dees
Assistant Examiner—Deborah D. Carr
Attorney, Agent, or Firm—Howard L. Rose

[57] ABSTRACT

A composition for reshaping hair including *Caesalpinea tinctoria* pod extract, a source of cupric ions and a source of chloride ions which is formulated into a thixotropic paste or cream for direct application to hair, subjecting the hair to the composition for a selected time, washing, setting and drying the hair, in the desired shape.

13 Claims, No Drawings

NATURAL EXTRACT BASED HAIR RESHAPING COMPOSITION

TECHNICAL FIELD

This invention relates to hair styling involving reshaping or "perming" and particularly to compositions and methods employing an extract of the pod of Caesalpinea tinctoria.

BACKGROUND OF THE INVENTION

Reshaping and relaxing human hair constitutes a substantial portion of the cosmetic/ beautician industry. Huge sums of money are spent on compositions and services in salons and in the home.

Hair is a proteinaceous material composed of α-keratin which includes in various amounts, sulfur bonds which contribute to the macroscopic shape of a strand. Reshaping or "perming" hair generally involves breaking the naturally occurring bonds and reforming the bonds to achieve a desired result. This may be accomplished by heat to a certain extent, but for long-term shape retention chemical treatment is preferred.

In the context of conventional materials used for the reshaping of hair commonly referred to as giving "a permanent", here are two broad classes. The first includes malodorous thio-alcohol/acid derivatives such as thioglycolic acid, thiopropionic acid, monothioglycerol, etc Treatment includes a rinse step with an appropriate oxidizer in a carefully controlled application.

The second general treatment involves the use of relatively strong caustic alkaline solutions formed from hydroxides of alkali and alkaline earth elements such as sodium hydroxide, calcium hydroxide, etc. With such treatment, it is necessary to further treat the hair with a neutralizing wash to obtain a physiologically compatible pH. It is known in the cosmetic industry that both of the above-specified treatments are harsh and may adversely affect the scalp or, if employed improperly, the hair itself. For example, the "neutralizing" step requires careful application in order to prevent exposure of the hair to too much or too little of the appropriate reagents.

SUMMARY OF THE INVENTION

It is an object of this invention to provide a novel composition and method for using same for reshaping living or cut hair.

It is another object of this invention to provide a composition for reshaping hair which is less harsh than conventional materials on the hair and scalp during treatment.

Still another object of this invention is to provide a composition and method for relaxing and configuring the rigid secondary structure of hair absent the use of caustic or harsh reagents.

Yet another object of this invention is to utilize a readily available, inexpensive natural product extract which is easily employed either by an individual at home or by a professional in a salon.

A further object of this invention is to provide effective hair treatment that permanently shapes hair without reducing tensile strength, softness or luster thereof and simultaneously dyes the hair black.

These and other objects are satisfied by a composition of matter for shaping hair comprising, Caesalpinea tinctoria pod extract, a source of cupric ions, and a source of chloride ions.

Other objects are satisfied by a method of reshaping hair comprising the steps of, providing a composition composed of Caesalpinea pod extract, a source of cupric ions and a source of chloride ions which may be ammonium chloride, combining the composition with a desired amount of water to provide a thixotropic paste, a thickening agent may also be added, applying the wetted composition to hair and maintaining the composition on the hair for a desired period of time, washing the composition from the hair and drying the hair.

The instant invention utilizes the discovery that the extract of the Caesalpinea tinctoria pod, a material employed for tanning animal skins and ink manufacturing, will relax and dye hair. The pod is produced by the Caesalpinea tinctoria tree, native to tropical South America, which is a member of the family Leguminosae. The extract, when combined with cupric and chloride ions, has now been found to provide an excellent relaxer and softener for existing tight, curly hair (new growth, of course, will not be altered) for permanently shaping and softening the hair. The composition also acts as a dye to darken the hair.

Since the pod extract is derived from a common plant, it is plentiful and inexpensive. Furthermore, it provides a less obnoxious alternative to the well known, disagreeable smelling thio compounds based "permanent" treatments. Also, in the context of adverse physiological affects occasioned by conventional use of strong alkaline compositions, since the instant composition is effective in a neutral or slightly acidic media, the potential for irritation, burns or allergic reaction, is minimized.

The invention should become readily apparent to a person having ordinary skill in the art given the detailed disclosure thereof contained herein.

DETAILED DESCRIPTION OF THE INVENTION

The composition and treatment of the instant invention employs Caesalpinea tinctoria pod extract combined with cupric and chloride ions. The composition, most conveniently, is formulated and applied as a paste or cream but may be formulated as a powder to which water is added.

In its simplest form, the composition is prepared by dissolving a cupric salt (cupric chloride) and ammonium chloride in the liquid pod extract. A thixotropic paste of the liquid is readily obtainable by adding an appropriate amount of starch. The pod extract is prepared by soaking or percolating comminuted pods in heated water. Once an appropriate concentration is achieved which depends on the time and temperature of the extraction step, the solution is filtered and the concentration adjusted, if necessary, by evaporation. If powdered extract is preferred, the solution is evaporated and then spray-dried by conventional techniques.

The following examples define with specificity the formulation of two compositions and corresponding treatments contemplated by this invention.

Example 1 (Cream or Paste)

To 4,5 kg of liquid Caesalpinea tinctoria pod extract with 500 g of solids per kg, 80 kg of water, 13,5 kg of corn starch, 1,0 kg of cupric chloride dihydrate, and 1,0 kg of ammonium chloride are added under agitation and the mixture heated to a temperature of 80° C. The resulting creamy paste is cooled until room temperature. A firm paste is obtained, which is packed in plastic sachets of 200 g net weight. The content of one sachet is diluted with a small quantity of water in order to obtain the desired consistency and the cream is applied thoroughly to curled hair, which is then covered with a plastic cap for 30 minutes. Subsequently, the hair is washed with shampoo and stretched on large bobs. After drying, the hair is black, lustrous, and less curly, remaining so permanently.

Example 2 (Powder)

To 13,5 kg of powdered, spray-dried *Caesalpinea tinctoria* pod extract, 73 kg of soluble tapioca starch, 8,0 kg of powdered cupric sulphate pentahydrate, and 5,5 kg of ammonium chloride are added, mixed thoroughly, sifted and packed in sachets of 35 g net weight. The content of one sachet is combined with 200 ml of cold water and mixed until a smooth cream of desired consistency is obtained. The cream is then applied thoroughly to a straight, dark, long hair, which is then covered with a plastic cap for 45 minutes. The hair is then washed and rolled on medium-size bobs. After drying, the black dyed hair exhibits a gentle permanent wave.

The treatments, two of which are identified above, fall within the generalized application steps which include thoroughly plastering the hair with the paste-like composition and covering the hair with a plastic cap for 30–60 minutes. The resident time is selected to achieve the desired degree of relaxation. Once the appropriate time has passed, the cap is removed and the hair washed with ordinary shampoo and cream rinse. The hair is then allowed to dry while subject to appropriate shaping means (curlers, bobs, wrapping, etc.). For example, if complete straightening is the objective, then the hair should be stretched around the head and pinned. Alternatively, if smooth undulating hair is desired then the hair should be rolled onto large hair bobs. As noted above, the composition dyes the hair resulting in a deep lustrous black color. Also, repeated treatment maintains the selected shape and color while effectively reshaping any new growth.

While described generally in the context of living hair, the treatment is equally effective for cut hair, preferably human, used for wigs and the like.

Given the foregoing, many variations and modifications of compositions and treatments should now be apparent to the skilled artisan. Accordingly, those variations and modifications are intended to fall within the spirit and scope of this invention as defined by the following claims:

I claim:

1. A composition for shaping hair, comprising: *Caesalpinea tinctoria* pod extract, a source of cupric ions, and a source of ammonium chloride ions.

2. A composition according to claim 1 where the pod extract is aqueous and the cupric ion source is obtained from a salt selected from the group consisting of cupric chloride, cupric chloride dihydrate, cupric sulphate pentahydrate and cupric sulphate.

3. A composition according to claim 1 further comprising a thickening agent.

4. A composition according to claim 2 further comprising a thickening agent.

5. A composition according to claim 1 where the pod extract is a concentrated aqueous extract from soaking comminuted pods in heated water.

6. A composition of matter, comprising
   4.5–13.5 kg *Caesalpinea tinctoria* pod extract,
   13.5–73 kg of a vegetable starch,
   1–8.0 kg of a cupric ion source, and
   1–5.5 kg of a chloride ion source including ammonium chloride.

7. A composition of matter according to claim 6 further including sufficient water to provide a thixotropic paste.

8. A method for shaping hair, comprising the steps of:
   providing a composition composed of Caesalpinea pod extract, a source of cupric ions and a source of chloride ions,
   combining the composition with a desired amount of water to form a wetted compositions,
   applying the wetted composition to hair and maintaining the wetted composition on the hair for a desired period of time,
   washing the wetted composition from the hair,
   drying the hair, in the desired shape, and
   covering the hair with a cap for 30–60 minutes after the wetted composition has been applied.

9. A method according to claim 8 further comprising the step of setting the hair with large curling bobs.

10. A method according to claim 11 further comprising the step of soaking comminuted *Caesalpinea tinctoria* pods in heated water, filtering the solution and evaporating the filtrate.

11. A method according to claim 10 further including the steps of adding water to the composition, heating the composition during mixing, adding a starch source to the mixture and cooling the mixture.

12. A method according to claim 10 further including the steps of:
   spray drying the pod extract,
   mixing starch into the composition to obtain a powder,
   sifting the powder mixture, and
   adding water to the mixture to obtain a cream-like consistency.

13. A method according to claim 8 further including the step of cutting hair and reshaping the cut hair.

* * * * *